United States Patent
Römisch et al.

(10) Patent No.: US 6,479,245 B1
(45) Date of Patent: *Nov. 12, 2002

(54) MONOCLONAL ANTIBODY WHICH IS SPECIFIC FOR ACTIVATED COAGULATION FACTOR VII, AND ITS USE

(75) Inventors: Jürgen Römisch, Marburg; Wiegand Lang, Cölbe; Annette Feussner; Joachim Röder, both of Marburg, all of (DE)

(73) Assignee: Aventis Behring GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/234,504

(22) Filed: Jan. 21, 1999

(30) Foreign Application Priority Data

Jan. 22, 1998 (DE) .......................... 198 02 139

(51) Int. Cl.⁷ ............................... G01N 33/53
(52) U.S. Cl. ................... 435/7.1; 530/387.1; 530/388.1
(58) Field of Search ............... 435/7.1, 7.95; 530/387.1, 388.1

(56) References Cited

U.S. PATENT DOCUMENTS 5,506,134 A * 4/1996 Soule et al.
5,681,722 A * 10/1997 Newman et al.
5,843,442 A * 12/1998 Soule et al.
6,221,659 B1 * 4/2001 Soule et al.

OTHER PUBLICATIONS

Philippou et al. Blood, vol. 89, pp. 767–775, Feb. 1997.*
Hirsch et al. Hemostasis & Thrombosis. Churchill Livingstone, New York, pp. 92–93 and 5–10, 1979.*
Harlow et al. antibodies, A Laboratory Manual, Chapter 14, Cold Spring Harbor, 1988.*

Harlow et al. Antibodies, A Laboratory Manual. Cold Spring Harbor Laboratory, pp 497 USA, 1988.*

Bending, M. Humanization of Rodent Monoclonal Antibodies. Methods: A Companion to Methods in Enzymology, 8:83–93, 1995.*

EMBASE Accession No. 95011879. Rao et al. Blood. 1995, 85/1, pp 121–129. Abstract.*

Campbell, A. M. Monoclonal Antibody Technology. Elsevier Sci. Publ. Amsterdam, The Netherlands & NY, NY, 1985, pp. 1–32.*

* cited by examiner

Primary Examiner—Patrick J. Nolan
Assistant Examiner—Amy DeCloux
(74) Attorney, Agent, or Firm—Finnegan, Henderson, Farabow, Garrett and Dunner, L.L.P.

(57) ABSTRACT

A monoclonal antibody has been developed which only specifically binds activated factor VII, and not factor VII, and which does not bind to an activated factor VII which is complexed with antithrombin III. This monoclonal antibody is isolated from the hybridoma cell line DSM ACC 2332. It can be used for qualitatively and quantitatively detecting factor VIIa in body fluids, blood coagulation preparations or the intermediate stages in the production of these preparations, on cell surfaces or in tissues, and can also be used as a humanized monoclonal antibody in therapeutic preparations.

9 Claims, 2 Drawing Sheets

MONOCLONAL ANTIBODY WHICH IS SPECIFIC FOR ACTIVATED COAGULATION FACTOR VII, AND ITS USE

The invention relates to a monoclonal antibody which specifically binds the activated coagulation factor VII (FVIIa), and to its use.

Blood coagulation is a complex system in which proteins are involved in the form of proteases, accelerators and inhibitors. Most of the proteases are present in a non-activated state. When coagulation is triggered, their proforms are converted into the activated state, resulting in the factors being activated in a cascade-like manner and the reaction thereby being amplified. The so-called intrinsic and extrinsic coagulation pathways differ fundamentally. When tissue is injured, the extrinsic cascade is initiated by thromboplastin (TF=tissue factor) becoming exposed on cell surfaces and binding the coagulation factor VII (FVII) or FVIIa. FVII is either activated autocatalytically on TF or by way of proteases such as thrombin or FXa. The TF/VIIa complex activates FX to give FXa, with the subsequent activation of prothrombin in turn taking place on phospholipid surfaces in the presence of calcium. This reaction is accelerated by FVa and leads, by way of the resulting thrombin, to the formation of fibrin and thereby wound closure.

Although the blood coagulation factors are normally present in a non-activated state, small quantities of FVIIa have been detected in the plasma of healthy individuals. This mechanism is possibly used so that it is physiologically possible to react very rapidly to very small tissue injuries when TF becomes exposed. A correlation of circulating, elevated FVIIa levels might play a role in pathophysiological reactions and induce these reactions, that is lead, for example, to an increased risk of thrombosis.

Coagulation tests which, because of the way they have been conceived, also measure traces of FVIIa, that is are unable to differentiate between FVII and FVIIa, are presently available for quantitatively determining FVII. A far more specific test system for determining FVIIa has been introduced in the form of the so-called rTF-FVIIa test. This system operates particularly reliably when no other activated factors, such as FXa or FIIa, or only small quantities of these factors are present. However, when higher concentrations of activated factors are present, the system can falsely indicate that FVIIa levels are elevated.

Apart from quantitatively determining factor VIIa in body fluids, particularly in plasma, it is also of great interest to determine FVII- and/or FVIIa-containing coagulation products. For example, so-called prothrombin complex concentrates (PPSB) are administered to patients who are suffering from deficiencies in the corresponding factors (FII/FVII/FIX/FX, etc.). Although it has not been possible to demonstrate that the presence of traces of FVIIa increases the risk of thromboembolic complications, efforts are made to ensure that the content of FVIIa in non-activated PPSB concentrates is as low as possible. The analysis in this regard is consequently of considerable interest. In addition, complex concentrates which are already activated are employed for certain indications, with it being necessary to quantify the activated factors carefully in this case as well.

Apart from the rTF-FVIIa assay, which measures the activity of the FVIIa, it is also desirable to have a system for detecting FVIIa antigen. The invention was consequently based on the object of providing a method for detecting FVIIa on an antigen basis.

This object is achieved by a monoclonal antibody which binds the activated factor VII specifically.

In order to prepare this antibody, mice were immunized with recombinant, activated factor VII. The mouse spleen cells were then fused with the murine myeloma cell line Sp2/0-Ag14. Polyethylene glycol 4000 was used as the fusion reagent. The cells were distributed on 24-well culture plates. The medium employed was Dulbecco's mod. Eagle's medium containing 10% fetal calf serum, and HAT medium was employed for the selection. After about 2 weeks, the growing cell lines were transferred to the wells of a 48-well plate and coded. The culture supernatant was then taken from approx. 2400 cell lines which had been grown and tested by ELISA for the presence of mouse IgG.

392 mouse IgG-positive cell lines were tested for specificity using immobilized factor VII and activated factor VII (ELISA). Of the tested cell lines, 1 cell line, having the code number 1069/1373, was identified as being specific for the activated factor VII. This cell line has been deposited in the German Sammlung für Mikroorganismen und Zellkulturen GmbH, Mascheroder Weg 1b, D-38124 Braunschweig, on Nov. 11, 1997 [Collection of Microorganisms and Cell Cultures] under No. DSM ACC 2332. The specificity of the antibody formed by this cell line was confirmed in the so-called BIAcore system. The purified monoclonal antibody is of the IgG 1 type.

The novel monoclonal antibody was further characterized by testing its ability to inhibit activated factor VII in a coagulation test. In this connection, it was found that the activity of the activated factor VII was inhibited by incubation with monoclonal antibody (Mab) 1069/1373 in a concentration-dependent manner. SDS-PAGE carried out on factor VII and activated factor VII, with subsequent transfer to nitrocellulose and incubation with Mab 106911373, confirmed that it was only activated factor VII, and not factor VII itself, which was bound and which led to corresponding labeling of the band when POD-coupled goat anti-mouse antibody and an appropriate substrate were added.

An additional feature of Mab 106911373 is that it is, in particular, free, activated factor VII which is recognized; i.e. there is no binding of activated factor VII which is complexed, for example, with antithrombin III (ATIII). The following experiment clarifies this property:

Complexes such as these are prepared in-vitro by incubating activated factor VII with an excess of antithrombin III/heparin at 4° C. for several hours. Depending on the extent to which the formation of the complex between activated factor VII and antithrombin III is complete, the activated factor VII is either markedly reduced or not detectable at all in the corresponding activity test. In this experiment, the activity of the activated factor VII was observed to decrease by more than 90% as compared with a control. A signal which was altered in a corresponding manner was found in the antigen detection system. This makes it clear that it is only free activated factor VII, and not the protease inhibitor complex, which is recognized. Mab 1069/1373 is outstandingly suitable for qualitatively and quantitatively detecting activated factor VII in solutions, such as body fluids, or in dissolved coagulation preparations or intermediates which arise during the preparation of blood coagulation factors. Example 1 (see below) describes the setting up of an appropriate ELISA test. In addition to this, the novel monoclonal antibody 1069/1373 is also suitable for detecting the binding of activated factor VII to cell surfaces and tissues. Known methods, such as the direct reaction of the Mab with activated factor VII or an indirect detection using a second (anti-mouse) antibody which is directed against the Mab, can be employed for the detection. Antigen-binding fragments of the novel monoclonal antibody which contain the activated factor VII-binding regions, such as F(ab2) or F(ab), can also be used for this purpose. Because of its inhibitory potential, a corresponding, humanized monoclonal antibody can, apart from the Mab and its fragments, be particularly advantageously used prophylactically and/or therapeutically, in particular for preventing or treating thrombotic events. A humanized monoclonal antibody of this nature comprises the activated factor VII-binding hypervariable regions of the novel monoclonal antibody and the framework regions of the variable and constant regions of the light and heavy chains of a human antibody.

In addition, the Mab can also be used for removing activated factor VII from solutions. For example, an affinity gel on which the novel monoclonal antibody is anchored can be prepared by coupling the antibody to known matrices such as BrCN Sepharose or protein A Sepharose. If the activated factor VII-containing solution is then passed through such a matrix, the activated factor VII is then bound to it selectively. This results in a coagulation preparation which is free from activated factor VII.

The invention is clarified by the following examples:

EXAMPLE 1
Use of Monoclonal Antibody 1069/1373 for Setting up an ELISA for Quantitatively Determining Activated Factor VII An indirect ELISA was developed for quantitatively determining activated factor VII: monoclonal antibody 1069/1373, which is specific for activated factor VII, was bound by adhesion to the wells of a microtiter plate. Bovine serum albumin was used for saturating unoccupied binding sites on the solid phase. The activated factor VII in the samples binds to the specific antibody. Unbound activated factor VII is removed by means of washing steps. An enzyme-labeled monoclonal antibody which is specific for factor VII is used as the second antibody. The bound activated factor VII is detected by means of a color reaction which is catalyzed by the enzyme which has been introduced.

Figure 1:
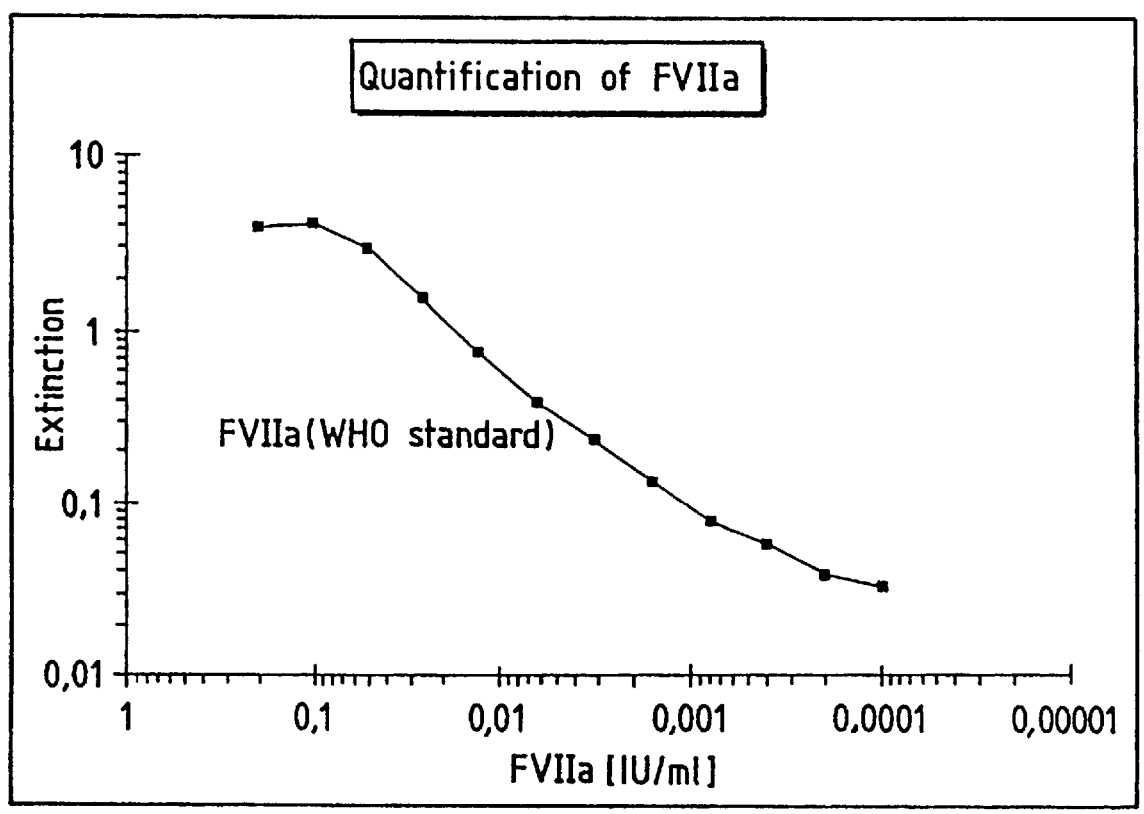
FIG. 1: WHO standard concentration curve for FVIIa

The contents of activated factor VII in sample solutions, for example plasma or products which are isolated from it, can be determined using the standard curve depicted in FIG. 1. The specificity of this test for activated factor VII, and its usability, were demonstrated by adding purified activated factor VII to factor VII or to plasma (after subtracting baseline values) and subsequently quantifying activated factor VII.

Figure 2:
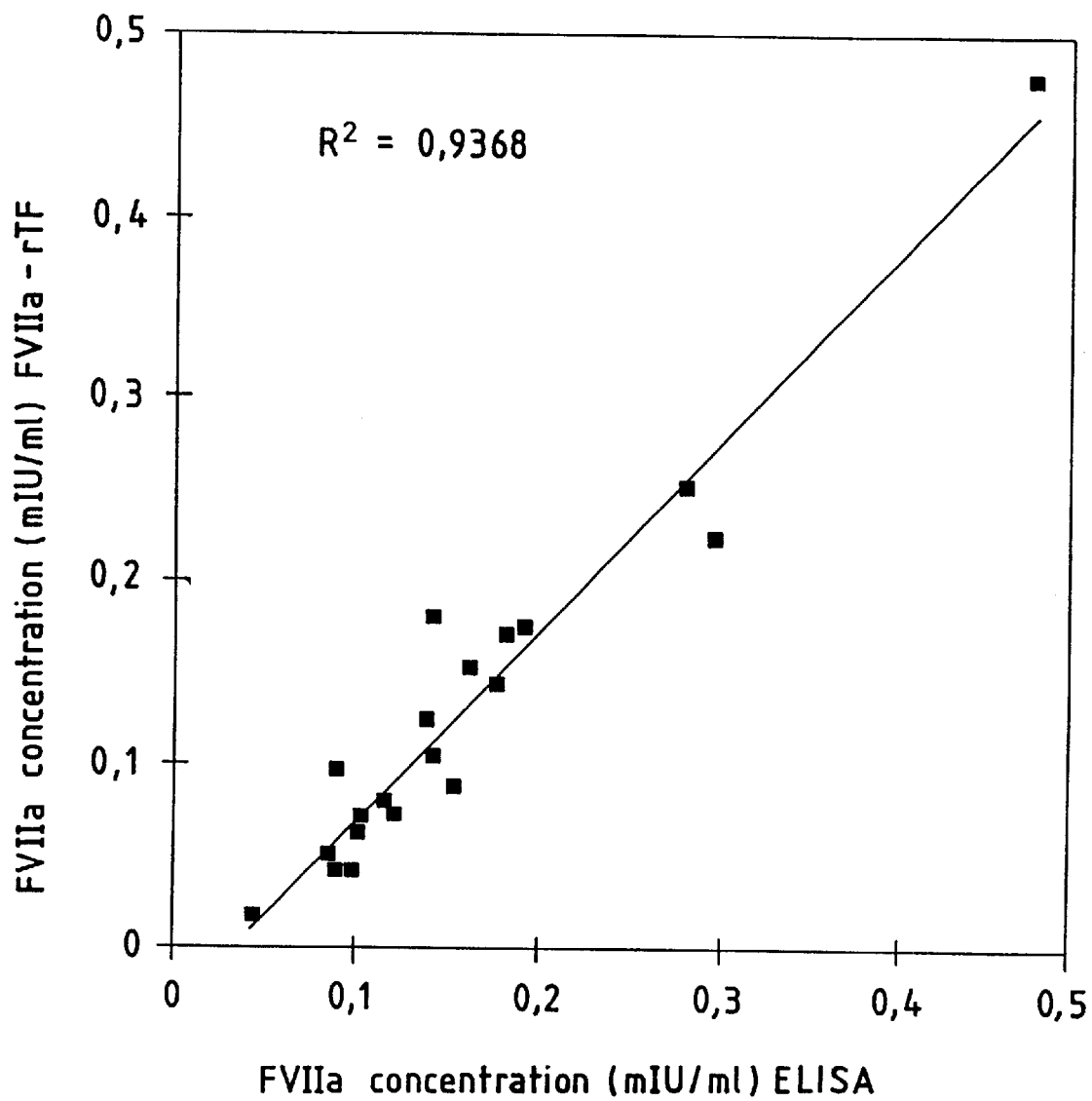
FIG. 2: Correlation of the concentration of FVIIa in 20 healthy donors utilizing the ELISA of the claimed invention as compared to the FVIIa/rTF test.

The ELISA which had been set up was used to measure the concentrations of activated factor VII antigen in plasmas from 20 healthy donors. The concentrations of activated factor VII which were determined were compared with concentrations which were ascertained using the FVIIa activity test (SATCLOT® FVIIa/rTF from Boehringer Mannheim/Stago). FIG. 2 shows that there is a very good correlation between the results obtained with the two test systems.

In addition, the ELISA was used for adding a defined quantity of activated factor VII to a solution which was obtained from plasma fractionation and which contained a large number of proteins and for quantifying the FVIIa concentrations before and after making the addition. Table 1 shows the FVIIa content of the plasma fraction (PF) before adding a defined quantity of rFVIIa, and also the analysis of the added rFVIIa solution and of the (PF+rFVIIa) mixture. The excellent recovery obtained underlines the suitability of the test for use with such complex protein solutions as well.

TABLE 1

| Sample | FVIIa antigen concentration (IU/ml) | |
|---|---|---|
| | Mean value | Standard deviation |
| rFVIIa | 5.02 | 0.19 |
| PF | 9.53 | 0.17 |
| PF + rFVIIa | 14.31 | 0.42 |

EXAMPLE 2
Use of Monoclonal Antibody 106911373 for Setting up an Immunoaffinity Matrix for Isolating/eliminating Activated Factor VII Purified monoclonal antibody 1069/1373 was bound to a sample of BrCN Sepharose. A plasma fractionation intermediate which contained the coagulation factors FII, FVII, FIX and FX, inter alia, and which had been supplemented with a defined quantity of purified factor VIIa was then pumped through this Mab-Sepharose. The solutions and column were equilibrated in 50 mM Tris, 150 mM sodium chloride, 10 mM calcium chloride, pH 8.5. The column flowthrough was collected. After the column material had been washed with equilibration buffer containing 0.5 M sodium chloride, the matrix was eluted with a buffer comprising 50 mM sodium citrate, 100 mM sodium chloride, pH 3.5.

The contents of the abovementioned coagulation factors in the starting material, the column flowthrough and the eluate were determined quantitatively by means of coagulation tests. The activated factor VII was quantified using the FVIIa/rTF test (STACLOT®, Boehringer Mannheim, Stago).

Result:
The affinity matrix eliminated the activated factor VII from the starting solution. Active factor VII was detected in the eluate from the column. The other coagulation factors which were tested for were found in the column flowthrough. This demonstrates that the novel monoclonal antibody can be used for specifically isolating and eliminating the activated factor VII. Activated factor VII which has been isolated in the eluate is present in active form and is then available for other applications.

What is claimed is:

1. A process for detecting activated factor VII in a sample comprising:
   (1) adding a monoclonal antibody which specifically binds to and inhibits the proteolytic activity of activated factor VII, and
   (2) detecting the complex formed between activated factor VII and said antibody
   wherein the monoclonal antibody is selected from the group consisting of:
      (i) a monoclonal antibody produced by the hybridoma cell line DSM ACC 2332; and
      (ii) an antigen binding fragment of a monoclonal antibody produced by the hybridoma cell line DSM ACC 2332.

2. The process as claimed in claim 1, wherein a color reaction is used for detecting the complex formed.

3. The process as claimed in claim 1, wherein the detection is a direct detection of the complex formed.

4. The process as claimed in claim 1, wherein the detection is an indirect detection, which detects a second antibody directed against the monoclonal antibody which specifically binds activated factor VII.

5. The process as claimed in claim 1, wherein the antigen binding fragment of the monoclonal antibody comprises the region which binds for activated factor VII.

6. The process as claimed in claim 1, wherein the sample is a solution.

7. The process as claimed in claim 6, wherein the solution is a body fluid, a blood coagulation preparation, or an intermediate of a blood coagulation preparation.

8. The process as claimed in claim 1, wherein the monoclonal antibody is a humanized monoclonal antibody comprised of the activated factor VII binding hypervariable regions of the monoclonal antibody and the framework regions of the variable and constant regions of light and heavy chains of a human antibody.

9. A process for determining the amount of activated factor VII in a sample comprising:
   (1) binding a monoclonal antibody to a microtiter plate wherein said monoclonal antibody specifically binds to and inhibits the proteolytic activity of activated factor VII;
   (2) saturating the unoccupied microtiter plate binding sites with a protein;
   (3) contacting the sample to the microtiter plate;
   (4) removing the unbound activated factor VII by washing; and
   (5) adding an enzyme-labeled monoclonal antibody, which is specific for factor VII, to determine the amount of activated factor VII in a sample
   wherein the monoclonal antibody bound to the microtiter plate in step (1) is selected from the group consisting of:
      (i) a monoclonal antibody produced by the hybridoma cell line DSM ACC 2332; and
      (ii) an antigen binding fragment of a monoclonal antibody produced by the hybridoma cell line DSM ACC 2332.

* * * * *